United States Patent [19]

Klothen

[11] 4,447,421

[45] May 8, 1984

[54] PROCESS FOR THE PREPARATION OF MEDICATED ANIMAL FEED SUPPLEMENT

[75] Inventor: Irving Klothen, Princeton, N.J.

[73] Assignee: American Cyanamid Company, Stamford, Conn.

[21] Appl. No.: 482,271

[22] Filed: Apr. 8, 1983

Related U.S. Application Data

[63] Continuation of Ser. No. 239,740, Mar. 2, 1981, abandoned, which is a continuation-in-part of Ser. No. 147,805, May 8, 1980, abandoned.

[51] Int. Cl.$^3$ .................... A61U 31/35; A61U 31/63; A61U 31/65; A61U 31/625
[52] U.S. Cl. ...................... 424/227; 264/117; 424/228; 424/229; 424/271; 424/283; 426/807
[58] Field of Search ............... 424/227, 271, 283, 228, 424/229; 426/807; 264/117

[56] References Cited

U.S. PATENT DOCUMENTS

| | | | |
|---|---|---|---|
| 2,703,285 | 3/1955 | Luther | 424/227 |
| 3,022,218 | 2/1962 | Sherman | 424/227 |
| 3,023,105 | 2/1962 | Upham et al. | 424/227 |
| 3,282,779 | 11/1966 | Pensack et al. | 424/227 |

*Primary Examiner*—Stanley J. Friedman
*Attorney, Agent, or Firm*—H. G. Jackson

[57] ABSTRACT

The invention is a process for the preparation of animal feed supplements containing various drugs or drug combinations, wherein uniformly potent particles of controlled particle size are obtained by the process, and the particles have been imparted a degree of hardness, sufficient to withstand shattering, abrasion or crumbling while in storage or being blended with feed, and thereby to minimize the retention of said drugs by the processing equipment. The invention also relates to a medicated animal feed supplement comprising a mixture of tetracycline antibiotics, sulfa drugs, penicillin antibiotics and whey solids.

12 Claims, No Drawings

PROCESS FOR THE PREPARATION OF MEDICATED ANIMAL FEED SUPPLEMENT

This is a continuation of Ser. No. 239,740, filed Mar. 2, 1981, which is a continuation-in-part of Ser. No. 147,805, filed May 8, 1980, both are now abandoned.

SUMMARY OF THE INVENTION

The invention is a process for the preparation of solid, particulated animal feed premixes, characterized by having a certain particle size and hardness range, wherein the premixes contain various drugs or micronutrients and other, pharmaceutically and nutritionally acceptable diluents, binders and formulation aids as needed, or desired.

Feed mills in which medicated animal feed premixes, supplements, concentrates or finished medicated animal feeds are prepared, have a tendency to retain some of the finely divided drugs due to electrostatic adhesion, dusting or some other phenomenon associated with the day-to-day operation of such installations. The retention of drugs within the mill is obviously undesired since it may, and usually does, result in the contamination of subsequent batches of nonmedicated animal feed or supplement prepared in said mill.

It is, therefore, the objective of the present invention to provide a method for the prevention of excessive build up, deposition, retention and/or dusting of a drug or mixture of drugs in a feed mill or in any other equipment used for the preparation of the above animal feed products, which would result in the contamination of same with said drugs while traversing said mill or other equipment in the course of being prepared; comprising: a process of compacting a drug or a mixture of drugs, optionally blended with a compressible, nutritionally acceptable and pharmaceutically inert diluent or diluent mixture, with sufficient force to obtain a compacted material of at least 10 kg to 30 kg hardness on a Stokes hardness tester and of a particle size range of 10 to 150 mesh.

The particles of the premixes obtained by the process of the present invention are designed to be of a size range large enough not to adhere to processing equipment surfaces (or to packaging surfaces) as for instance by electrostatic adhesion, or to be carried away in a dust collecting stream, and yet at the same time to be of an adequately small size range so that a statistically sufficient number of particles are present in the finished feed premix to assure uniform distribution throughout the batch of feed in which it is blended to achieve the desired drug concentration.

In general, conventional medicated animal feed premixes are prepared by blending finely powdered drugs (crude or pure) and/or micronutrients with pharmaceutically and nutritionally acceptable diluents or carriers to obtain drug concentrations in the premixes so that convenient quantities, e.g., 0.5, 1 or 2 lb (or kg) per ton of feed can be weighed out by the feed formulators. Unfortunately, in such premixes, the drug particles remain discrete and thus their distribution pattern is independent of the other ingredients of the premix. When blended with animal feed, wide particle size ranges or unexpected agglormeration may change this pattern from the one desired.

The difficulties encountered by using fine powders in medicated animal feed premixes has been recognized, and a number of attempts have been made to overcome them. Thus, such formulations have been aggregated on to the surface of coarse carriers by the use of suitable binders or sticking agents; while other attempts relate to the preparation of wet aggregates followed by granulation and subsequent drying of the granules. Unfortunately, these processes are less than satisfactory. The former process yields aggregates which do not adhere permanently, drying and attrition during storage and handling releases free, fine drug particles which again become subject to segregation, adhesion to surfaces and to removal as dust. The latter process is generally too costly for this type of application and also, because of the frequent use of water, causes stability problems with many drugs.

It is now found that by the process and composition of my invention, granular, medicated animal feed premixes can be prepared from any drug or combination of drugs by combining these with the necessary amount of a compressible, inert and pharmaceutically and nutritionally acceptable diluent, such as whey solids, in the absence of added water or any other liquid binder, followed by blending, compacting and granulating the composition under sufficiently mild conditions so as to avoid adiabatic overheating (caused by some extrusion processes) of the mixtures and thus prevent or minimize thermal decomposition of the components. Furthermore, since thorough blending precedes the compacting and granulation steps, the finished granules are of relatively uniform potency throughout, and having been compacted under pressure prior to granulation, the granules possess better resistance to crushing, crumbling and surface abrasion during storage and during blending with feed.

Consequently, more uniform distribution of drugs in the feed can be expected; and, in general, the feed premixes prepared by the process of the invention are useful for the distribution of any drug or microingredient in feedstuffs.

The process of the present invention is especially useful for the preparation of medicated premixes containing pure drugs, since these are, as a general rule, used in very small amounts and, in addition, are usually very fine in particle size and thus tend to be subject to various types of segregation from the feed matrix. Specifically, as stated above, the particulated compositions prepared by the process of this invention are of a size range so that adhering, and thus retention of the product in the blending conveying and compacting equipment, is minimized. Retention in said equipment would normally lead to the phenomenon known as drug carryover or cross-contamination.

Medicated feed premixes prepared by the process of the present invention comprise: about 5% by weight to about 65% by weight of composition, a finely divided drug or a mixture of drugs hereinbelow defined and described in detail and a compressible, nutritionally acceptable and pharmaceutically inert diluent or diluent mixture in amounts sufficient to total said composition to 100%.

Conveniently, by the process and composition of the invention, a medicated feed premix can be prepared by admixing an antibiotic such as Avoparcin, Bacitracin, Bambermycin, Griseofulvin, Hygromycin B, Lincomycin, Monensin, Neomycin, Nystatin, Oleandomycin, Streptomycin, Tylosin and salts thereof, Virginiamycin or a tetracycline antiobiotic such as tetracycline, chlortetracycline, oxytetracycline or dimethylchlortetracycline and mixtures thereof, either as the pure drugs or the fermentation solids containing the solids, a sulfa drug such as sulfamethazine, sulfaethoxypyridazine, sulfadimethoxine, sulfaquinoxaline, sulfathiazole or other suitable sulfa drugs, carbadox, thiabendazole, procaine penicillin G or other stable penicillin salts, an inert diluent which has been found to compact well, such as whey solids, lactose, sucrose, cellulose, ground oyster shells, calcium carbonate, dicalcium phosphate or mixtures thereof, and preferably whey solids. The mixture thus obtained is then thoroughly blended and fed into a set of compacting rolls which are under hydraulic pressure of from about 90 kg cm$^{-2}$ to about 212 kg cm$^{-2}$. The compacted material emerges from the rolls in various shapes such as briquettes, ribbed sheets and the like depending on the type of compacting rolls chosen. The emerging solid shapes possess a Stokes hardness range of from about 10 kg to about 30 kg in contrast to conventional granulated feed premixes having a hardness range of from about 5 kg to 8 kg. Finally, the material thus obtained is ground or fragmented by suitable means to the desired particle size range, usually from 10/40 to 40/150 mesh.

The above description of the process of the invention suggests compositions comprising at least one of each of the antibiotics selected from the group defined above, a sulfa drug, carbadox or thiabendazole and a penicillin antibiotic as the active components of said composition. It should be clearly understood, however, that the above process can be used successfully to prepare medicated feed premixes having the above described desirable characteristics, but containing only one of the above described drugs, especially sulfa drugs.

Thus, for instance, 25% by weight to about 35% by weight of composition of chlortetracycline fermentation solids comprising: chlortetracycline calcium complex, mycelial solids, nutrient residues and filteraid, and containing 10% by weight to about 25% by weight of chlortetracycline; 2% to 10% by weight of formulation of sulfamethazine, 2% to 10% by weight of procaine penicillin G and sufficient amount of whey solids to total the mixture to 100%, are mixed. The above whey solids have the following composition:

| | |
|---|---|
| Lactose, % | 50–67.7 |
| Protein, % | 12.1–17.2 |
| Minerals, % | 9.6–15.6 |
| Fat, % | 0.75–1.0 |
| Moisture, % | 4.5–6.0 |
| Fiber, % | — |
| Calcium, % | 0.8–1.5 |
| Phosphorus, % | 0.7–1.0 |
| Riboflavin, mg/kg | 24.25–52.91 |
| Niacin, mg/kg | 11.02–17.64 |
| Thiamine, mg/kg | 3.97–4.85 |
| Panthotenic acid, mg/kg | 48.5–74.96 |
| Choline, mg/kg | 2,425.08–4,188.78 |
| Pyridoxine, mg/kg | 2.87–5.29 |
| Vitamin $B_{12}$, mmg/kg | 26.1–33.07 |
| Folic Acid, mmg/kg | 132.28–253.53 |
| Biotin, mmg/lb | 352.74–595.25 |

It is recognized, of course, that there may be variations in the composition of whey solids depending on their origin. It is not expected, however, that such variations would significantly alter or otherwise affect the process of the present invention and the results obtained thereby.

The mixture is then thoroughly blended and fed into a pair of compacting rolls which are under a hydraulic pressure of from about 90 kg cm$^{-2}$ to about 212 kg cm$^{-2}$, and finally, the shaped, compacted material is ground and sifted to a particle size range of from 10 to 150 mesh, and preferably 16/60 mesh.

Similarly, by the above procedure, medicated feed premixes are prepared, comprising 10% to 100% by weight of composition of a sulfa drug selected from sulfamethazine, sulfaethoxypyridazine, sulfathiazole or other suitable sulfa drugs and mixtures thereof; and when the amount of said drugs is less than 100% an inert diluent or mixture of diluents, selected from the group hereinabove described, in amounts sufficient to total said premix to 100%.

It is recognized, of course, that the above process may be utilized in the preparation of medicated feed premixes containing drugs and antibiotics other than those listed above, and that additives such as antistatic agents, coating agents and drying agents may be incorporated in the premixes, if so desired.

The medicated premixes prepared by the process of the invention are designed to allow incorporation of about 100 g of tetracycline antibiotic, of about 100 g of sulfa drug and of about 50 g penicillin per ton of feed.

The process can easily be changed to accomodate any other desired drug concentration by varying the concentration of the drug in the feed premix or by changing the accepted particle size range so that an adequate number of particles of compacted premix per ton of feed are introduced to assure statistically uniform distribution.

The following non-limiting Examples are provided to further illustrate the invention.

EXAMPLE 1

Preparation of medicated granular feed premixes having the composition of the invention Medicated feed premix batches are prepared, having the composition and size as given in Table I below.

The components are mixed and blended for 10 minutes in a ribbon blender. The blended composition is then fed to 2.5 cm (1") wide briquetting rolls of 12.7 cm (5" diameter) at a predetermined pressure and rate to yield briquettes or ribbons having a range of desired hardness. These compacts are then ground and sieved to 26/60 mesh and <60 mesh fractions. Table II below lists the number of batches prepared, the compacting roll pressures used and the degree of hardness achieved.

For comparison, a sample of a standard, medicated premix having the same composition, except for the diluent is compacted, and the pertinent data entered as No. 14 in Table II below, wherein it can be clearly seen that the composition of the present invention yields much harder material than comparable, conventional blends.

TABLE I

Composition and size of medicated feed premixes of the present invention

| | % by weight | | | drug | | |
|---|---|---|---|---|---|---|
| Component of Composition | % Purity | % of composition | g per batch | g = real per batch | g/kg of formulation | g/lb of formulation |
| Chlortetracycline fermentation | 15.4 | 32 | 1,600 | 249.9 | 49.4 | 22.4 |

TABLE I-continued
Composition and size of medicated feed premixes of the present invention

| Component of Composition | % Purity | % by weight of composition | g per batch | drug g = real per batch | g/kg of formulation | g/lb of formulation |
|---|---|---|---|---|---|---|
| Sulfamethazine | 100 | 4.6 | 230 | 230 | 46.0 | 20.9 |
| Procaine Penicillin G | 60 | 4.0 | 200 | 120 | 24.0 | 10.9 |
| Whey solids | | 59.4 | 2,970 | | | |
| Totals: | | 100.0 | 500 | | | |

| No | Feed Screw Pressure kg cm$^{-2}$ | Stokes Hardness kg |
|---|---|---|
| 1 | 94.5 | 25.5 |
| 2 | 94.5 | 25.9 |
| 3 | 122.5 | 29.6 |
| 4 | 154.0 | 26.3 |
| 5 | 189.0 | 30.0 |
| 6 | 189.0 | 28.5 |
| 7 | 189.0 | 25.5 |
| 9 | 189.0 | 23.3 |
| 10 | 189.0 | 19 |
| 11 | 210.0 | 15.8 |
| 12 | 210.0 | 26.5 |
| 13 | 94.5 | 22.5 |
| 14 | 94.5 | 7.5 |

EXAMPLE 2

Large scale preparation of medicated, granular feed premix having the composition of the invention By the method of Example 1, chlortetracycline fermentation solids (18.94% pure; 4,732 g as is material=26% by weight of composition), sulfamethazine (100% pure; 840 g=4.63% by weight of composition), procaine penicillin G (60% pure; 734 g=4.05% by weight of composition) and whey solids (11,837 g=65.52% by weight of composition) are blended and fed at a rate of 800 g/minutes and at 129.5 g kg cm$^{-2}$ pressure to 5 cm (2") wide 12.7 cm (5") diameter corrugated rolls to be compacted to the desired degree of hardness. Finally, the material is granulated to the desired mesh size range, 20 to 60 mesh.

The thus prepared premix provides:

| Ingredient | g/kg | g/lb |
|---|---|---|
| Chlortetracycline | 49.4 | 22.4 |
| Sulfamethazine | 46.3 | 21.0 |
| Procaine Penicillin G | 24.25 | 11.0 |

By the above method, excepting that calcium carbonate is substituted for whey solids, a medicated granular feed premix is prepared comprising:

| Ingredient | purity | % by weight of composition |
|---|---|---|
| Chlortetracycline fermentation solids | 15.4 | 64 |
| Sulfamethazine | 100 | 9 |
| Procaine Penicillin G | 60 | 8 |
| Calcium carbonate g.s. ad 100 | | 19 |
| Total | | 100 |

EXAMPLE 3

Preparation of medicated granular feed premixes containing sulfamethazine

Three medicated feed premix batches of approximately 90 kg (200 lb) each are prepared, having the following composition:

| Component | kg | lb |
|---|---|---|
| Sulfamethazine | 18.1437 | 40 |
| Oyster shell meal | 36.2874 | 80 |
| Whey solids, sweet | 36.2874 | 80 |
| Total: | 90.1785 | 200 |

The components are mixed and blended for 10 minutes in a ribbon blender. The blended compositions are then fed to 10.16 cm (4") wide rolls of 25.4 cm (10") diameter at a predetermined pressure and rate to yield ribbons exceeding 30 kg Stokes hardness rating. The compacted samples are ground and sifted to 16/80 and 30/80 mesh fractions.

EXAMPLE 4

Preparation of compacted, granular, sulfamethazine

A 20 g sample of sulfamethazine is compacted at 105.46 kg cm$^{-2}$ pressure. The compaction has an averaged (four measurements) Stokes hardness rating of 10.25 kg. The sample is ground and sifted to 60/100 mesh.

EXAMPLE 5

Preparation of medicated granular feed premixes containing 50% by weight of sulfamethazine Two medicated feed premix batches of 2,000 g each are prepared, having the following composition:

| Component | Wt in g | % by Wt of Composition |
|---|---|---|
| Sulfamethazine | 1,000 | 50 |
| Calcium Carbonate | 500 | 25 |
| Whey solids, sweet | 500 | 25 |
| Total: | 2,000 | 100 |

The components are mixed and blended for 10 minutes in a double cone blender, and are then compacted at 105.46 kg cm$^{-2}$ pressure. The thus obtained compactions have an averaged (three measurements, each) Stokes hardness rating of 18.7 kg and 16.0 kg, respectively. The samples are ground and sifted to 30/80 mesh.

EXAMPLE 6

Preparation of a medicated granular feed premix containing 10% by weight of sulfathiazole A 2,000 g sample of medicated granular feed premix is prepared, having the following composition:

| Component | Wt in g | % by Wt of Composition |
|---|---|---|
| Sulfathiazole | 200 | 10 |
| Whey solids, sweet | 1,000 | 50 |
| Calcium carbonate | 800 | 40 |
| Total: | 2,000 | 100 |

The components are mixed, blended, and are then compacted at 105.46 kg cm$^{-2}$ pressure. The compacted blend has a stokes hardness of 25.0 kg (average of three measurements). The sample is ground to 16/60 mesh.

EXAMPLE 7

Determination of drug carry-over in a commercial feed mill during the preparation of medicated feed supplements A total of 25 two-ton batches of medicated feed supplement crumbles are prepared using commercial equipment. Ten of these two-ton batches are prepared using standard medicated feed premixes while 15 of these two-ton batches are prepared from medicated feed premixes made by the method of the present invention.

The composition of the two-ton medicated feed supplement crumbles is as follows:

| Compound | Wt in lb | Wt in kg |
|---|---|---|
| Medicated feed premix* | 222.6 | 103.69 |
| Grain screenings | 1,800.0 | 816.47 |
| Alfalfa | 1,811.4 | 821.64 |
| Animal fat | 60.0 | 27.22 |
| Bond aid** | 100.0 | 45.36 |
| Totals: | 4,000.0 | 1,814.38 |

\* = composition of the medicated feed premixes is given in Table II.
\*\* = Sodium lignin sulfonate

TABLE II

| | Composition of medicated feed premixes | | | | | |
|---|---|---|---|---|---|---|
| | Standard Formulation | | | Granular, Compacted Formulation | | |
| Compound | As is, in g | % by Wt | g/lb | As is in g | % by Wt | g/lb |
| Chlortetracycline fermentation solids (15.43%) | 226.8 | 50 | 35 | 226.8 | 50 | 35 |
| Sulfamethazine (100%) | 35 | 7.72 | 35 | 35 | 7.72 | 35 |
| Oil, mineral | 9.08 | 2 | 9.08 | — | — | — |
| Soybean meal, q.s. ad 100 | 182.71 | 40.28 | 182.71 | — | — | — |
| Whey solids, q.s. ad 100 | — | — | — | 191.79 | 42.28 | 191.79 |

The preparation of the ten two-ton batches of medicated feed supplement crumbles is followed by a clean-out procedure during which extensive samples are obtained. The clean-out procedure comprises a 200 lb "wash" and two two-ton "flushes". The "wash" and the two "flushes" consist of an alfalfa-grain screenings mixture with fat. The 200 lb "wash" is discarded while the two two-ton flushes usually are stored for later use in the preparation of similar medicated feed additives. A similar clean-out procedure follows the preparation of the 15 two-ton batches of medicated feed supplement crumbles prepared from the granular compacted premixes of the present invention.

After flushing, the feed mill is used to prepare two three-ton blends of non-medicated feed pellets, and the flushings following same, are analyzed for sulfamethazine contamination. The data obtained are summarized in Table III below wherein it can be clearly seen that preparations using the granular, compacted feed premixes of the present invention decrease the sulfamethazine contamination two to ten fold compared to similar standard medicated feed premixes.

TABLE III

Determination of drug carry-over in a commercial feed mill during the preparation of feed supplements

| | | Sulfamethazine Contamination in ppm | |
|---|---|---|---|
| Cumulative Total Lbs of Feed Blended | Sample | Standard Formulation | Granular, Compacted Formulation of the Invention |
| 200 | 200 lb mixer flush | 337 | — |
| 4,200 | 1st two-ton flush of 25.2 | 215 | |
| | Mixing/conveying system | 37.0 | 6.5 |
| | | 40.7 | 3.2 |
| | | 39.2 | <3.2 |
| | | 35.4 | |
| | Tail of 1st two-ton flush | 579 | 17.8 |
| 8,200 | 2nd two-ton flush of mixing system | 40.7 | 5.2 |
| | | 27.7 | 2.3 |
| | | 12.7 | <1.6 |
| | | 9.5 | — |
| | Tail of 2nd two-ton flush | 11.8 | 6.6 |
| 14,200 | 1st three-ton non-medicated through mixing/conveying system | No samples | 8.6 |
| | | | 4.5 |
| | | | 1.2 |
| | Tail of 1st three-ton batch | | 7.3 |
| 20,200 | 2nd three-ton-non-medicated through mixing/conveying system | 6.7 | 1.6 |
| | | 4.1 | 1.6 |
| | | 4.7 | 1.6 |
| | | 5.1 | — |
| | | 5.7 | — |
| | Tail 2nd three-ton non-medicated blend | 80 | 8.0 |
| 24,200 | 1st two-ton flush of bagger and bagger bin | 35.8 | 21.8 |
| | | 14.2 | 16.1 |
| | | 6.9 | <1.5 |
| | | 3.7 | 3.0 |
| | | 4.0 | 20.5 |
| | | 24.5 | 1.4 |
| | Tail of 1st two-ton flush bagger | 80.0 | 3.0 |
| 28,200 | 2nd two-ton flush of bagger and bagger bin | 49.4 | 15.2 |
| | | 12.3 | 1.2 |
| | | 4.5 | 0.8 |
| | | 3.2 | 1.1 |

TABLE III-continued

Determination of drug carry-over in a commercial feed mill during the preparation of feed supplements

| Cumulative Total Lbs of Feed Blended | Sample | Sulfamethazine Contamination in ppm | |
|---|---|---|---|
| | | Standard Formulation | Granular, Compacted Formulation of the Invention |
| | | 1.3 | <0.8 |
| | Tail of 2nd two-ton flush of bagger | — | 14.2 |
| 32,200 | 3rd two-ton through bagging bin | 2.1 | 7.6 |
| | | <0.5 | 0.3 |
| | | <0.5 | 0.5 |
| | Tail or 3rd two-ton lot | 5.1 | — |
| | 200 lb pellet mill flush | 192 | 127 |

EXAMPLE 8

Determination of drug carry-over in a feed mill during the preparation of medicated feed supplements Medicated pig feed supplements are prepared in four trials, each using a standard 18% protein swine starter formula in combination with:
a. Standard medicated premix;
b. Compacted granular medicated premix;
c. Compacted granular sulfamethazine (100%), prepared by the method of Example 4;
d. Compacted granular sulfamethazine (20% by weight of formulation), prepared by the method of Example 3.

PROCEDURE

The drug premixes are incorporated each at a 25 lb per ton level in 4×1,000 lb batches, followed by one 1,000 lb non-medicaed swine feed which serves as a flush. The composition of these rations are shown in Table IV.

Upon completion of the trial runs, each is followed by the preparation of 20×1,000 lb of non-medicated poulty layer formula (composition appended to Example) which is passed through the mill and is bagged.

SAMPLING

All samples are taken from bags prior to final closure. Samples are taken from the 8th and 16th bags of each medicated swine ration blend. Samples are taken from bags 1, 4, 8, 12, 16 and 20 of the non-medicated swine ration flush. The poulty layer feed which follows the swine feed production is sampled as follows: batches 1 and 2 are sampled at bags 1, 4, 8, 12, 16 and 20, thereafter samples are taken only from bags 8 and 16.

The samples are analyzed and the amount of sulfamethazine present in the medicated and non-medicated feed supplements is determined. The results are shown in Table V, wherein it can be clearly seen that contamination of non-medicated feeds is markedly lower when compacted granular feed premixes or drugs are used, rather than the corresponding non-compacted standard formulations.

TABLE IV

| | Percent by weight composition of the medicated Feed supplement of the example | | | | |
|---|---|---|---|---|---|
| Component | Non-Medicated | Medicated standard "a" | Medicated granular "b" | Sulfamethazine - granular | |
| | | | | "c" | "d" |
| Soybean meal (44%) | 83.5 | 82.25 | 82.25 | 83.442 | 83.21 |
| Dicalcium phosphate | 6.0 | 6.0 | 6.0 | 6.0 | 6.0 |
| Limestone | 6.5 | 6.5 | 6.5 | 6.5 | 6.5 |
| Salt | 2.5 | 2.5 | 2.5 | 2.5 | 2.5 |
| Trace Minerals* | 0.5 | 0.5 | 0.5 | 0.5 | 0.5 |
| Vitamin premix** | 1.0 | 1.0 | 1.0 | 1.0 | 1.0 |
| Standard premix | — | 1.25 | — | — | — |
| Granular premix | — | — | 1.25 | — | — |
| Granular sulfamethazine (100% by wt) | — | — | — | 0.058 | — |
| Granular sulfamethazine (20% by wt) ("d") | — | — | — | — | 0.292 |

*= Analysis per lb:
Maganese, minimum 10%; Iron, minimum 10%; Zinc, minimum 10%; Calcium, maximum 5%, Calcium, minimum 4%; Copper minimum 1%; Iodine minimum 0.3%; Cobalt, minimum 0.1%.
Ingredients: Manganese sulfate, ferrous sulfate, ferrous carbonate, iron oxide, zinc sulfate, zinc oxide, calcium carbonate, copper oxide, potassium iodide, cobalt carbonate.
**=0 Analysis per lb:
Vitamin A 400,000 USP units; Vitamin $D_3$ 30,000 USP units; Vitamin E 2,000 I units, Riboflavin 450 mgs; Menadione ($K_3$) 155 mgs; d-Pantothenic acid 1,200 mgs; Niacin 2,500 mgs; Choline chloride 46,100 mgs; Vitamin $B_{12}$.
Ingredients: Vitamin A acetate, d-activated animal sterol, dl-alpha tocopheryl acetate, menadione sodium bisulfite complex, riboflavin supplement, calcium pantothenate, niacin, choline chloride, Vitamin $B_{12}$ supplement, calcium carbonate roughage products, mineral oil and ethoxyquin, (a preservative).

TABLE V

Determination of drug carry-over in a feed mill during the preparation of feed supplements

| Cumulative Total Lbs of Feed Blended | Sample | ppm Sulfamethazine found in feed supplement | | | |
|---|---|---|---|---|---|
| | | a | b | c | d |
| 1,000 | Medicated Swine Conc. Batch 1, Bag 16 | 431 | 517 | 497 432 | 782 741 |

TABLE V-continued
Determination of drug carry-over in a feed mill during the preparation of feed supplements

| Cumulative Total Lbs of Feed Blended | Sample | ppm Sulfamethazine found in feed supplement | | | |
|---|---|---|---|---|---|
| | | a | b | c | d |
| 2,000 | Medicated Swine Conc. Batch 2, Bag 16 | 373 | 500 | 467 480 | 674 584 |
| 3,000 | Medicated Swine Conc. Batch 3, Bag 16 | 356 | 514 | 379 508 | 646 683 |
| 4,000 | Medicated Swine Conc. Batch 4, | | | | |
| | Bag 1 | | 500 | 327 | 469 |
| | Bag 4 | 298;301 | 607 | 402 | 464 |
| | Bag 12 | 398;419 | | 449 | 705 |
| | Bag 16 | 369;377 | | 576 | 753 |
| | Bag 20 | | 594 | 1,868 | 822 |
| 5,000 | Nonmedicated Swine Conc. | | | | |
| | Bag 1 | — | 18.1 | 11.4 | 6.8 |
| | Bag 4 | 11.3 | 2.4 | | |
| | Bag 8 | 13.7 | 6.5 | 12.6 | 7.4 |
| | Bag 12 | 16.1 | 2.3 | | |
| | Bag 16 | 17.7 | 4.9 | 12.8 | 15.7 |
| | Bag 20 | — | 49.5 | 190.0 | 61.0 |
| 6,000 | Poultry Layer Feed Batch 1, | | | | |
| | Bag 1 | 19.4 | 3.8 | 11.3 | 7.2 |
| | Bag 11 | — | 5.0 | | |
| | Bag 12 | 20.2 | — | 12.8 | 5.0 |
| | Bag 20 | 175 | 6.8 | 66.6 | 51 |
| 7,000 | Poultry Layer Feed Batch 2, | | | | |
| | Bag 1 | 8.9 | 2.4 | 3.6 | 3.5 |
| | Bag 12 | — | 1.5 | 4.1 | 3.4 |
| | Bag 20 | 94.6 | 5.2 | 47.5 | 28 |
| 8,000 | Poultry Layer Feed Batch 3, | | | | |
| | Bag 8 | 21.8 | 0.5 | 2.7 | 2.8 |
| | Bag 16 | 6.1 | 1.2 | 3.9 | 1.9 |
| 9,000 | Poultry Layer Feed Batch 4, | | | | |
| | Bag 8 | 3.4 | 0.5 | 1.6 | 1.2 |
| | Bag 16 | 3.5 | <0.5 | 2.1 | 1.3 |
| 10,000 | Poultry Layer Feed Batch 5, | | | | |
| | Bag 8 | 3.5 | <0.5 | 1.6 | 1.0 |
| | Bag 16 | 44.9 | <0.5 | 2.5 | 1.4 |
| 11,000 | Poultry Layer Feed Batch 6, | | | | |
| | Bag 8 | 3.0 | <0.5 | 0.8 | 0.6 |
| | Bag 16 | 2.0 | <0.5 | 0.6 | 0.6 |
| 12,000 | Poultry Layer Feed Batch 7, | | | | |
| | Bag 8 | 1.0 | <0.5 | 0.5 | 0.6 |
| | Bag 16 | 1.3 | <0.5 | 1.1 | 0.6 |
| 13,000 | Poultry Layer Feed Batch 8, | | | | |
| | Bag 8 | 1.6 | <0.5 | 0.5 | 0.7 |
| | Bag 16 | 1.4 | <0.5 | 1.0 | 0.5 |
| 14,000 | Poultry Layer Feed Batch 9, | | | | |
| | Bag 8 | 0.7 | <0.5 | 0.5 | 0.6 |
| | Bag 16 | 0.8 | <0.5 | 0.7 | 0.7 |
| 15,000 | Poultry Layer Feed Batch 10, | | | | |
| | Bag 8 | 0.7 | <0.5 | 0.7 | 0.5 |
| | Bag 16 | 0.7 | 0.5 | 0.5 | 0.7 |
| 16,000 | Poultry Layer Feed Batch 11, | | | | |
| | Bag 8 | 0.7 | 2.2;2.8 | 0.7 | 0.6 |
| | Bag 16 | 0.6 | <0.5 | 0.5 | 0.6 |
| 17,000 | Poultry Layer Feed Batch 12, | | | | |
| | Bag 8 | 1.1 | <0.5 | 0.5 | 0.5 |
| | Bag 16 | 0.7 | <0.5 | <0.5 | 0.7 |
| 18,000 | Poultry Layer Feed Batch 13, | | | | |
| | Bag 8 | 0.5 | <0.5 | 0.5 | 0.7 |
| | Bag 16 | 0.8 | <0.5 | <0.5 | 0.5 |

TABLE V-continued
Determination of drug carry-over in a feed mill during the preparation of feed supplements

| Cumulative Total Lbs of Feed Blended | Sample | ppm Sulfamethazine found in feed supplement | | | |
|---|---|---|---|---|---|
| | | a | b | c | d |
| 19,000 | Poultry Layer Feed Batch 14, | | | | |
| | Bag 8 | 2.4 | <0.5 | <0.5 | 0.5 |
| | Bag 16 | 7.7 | <0.5 | 0.6 | 0.5 |
| 20,000 | Poultry Layer Feed Batch 15, | | | | |
| | Bag 8 | 173 | <0.5 | 0.9 | 0.5 |
| | Bag 16 | 2.9 | <0.5 | <0.5 | <0.5 |
| 21,000 | Poultry Layer Feed Batch 16, | | | | |
| | Bag 8 | 1.4 | <0.5 | <0.5 | <0.5 |
| | Bag 16 | 0.6 | <0.5 | 0.5 | 0.5 |
| 22,000 | Poultry Layer Feed Batch 17, | | | | |
| | Bag 8 | 0.5 | <0.5 | 0.5 | 0.5 |
| | Bag 16 | 0.6 | <0.5 | 0.5 | <0.5 |
| 23,000 | Poultry Layer Feed Batch 18, | | | | |
| | Bag 8 | <0.5 | <0.5 | <0.5 | 0.5 |
| | Bag 16 | 0.5 | <0.5 | <0.5 | 0.6 |
| 24,000 | Poultry Layer Feed Batch 19, | | | | |
| | Bag 8 | 0.6 | <0.5 | <0.5 | 0.5 |
| | Bag 16 | 0.6 | <0.5 | 0.6 | <0.5 |
| 25,000 | Poultry Layer Feed Batch 20, | | | | |
| | Bag 8 | 160 | <0.5 | 0.8 | <0.5 |
| | Bag 16 | 1.9 | <0.5 | 0.8 | <0.5 |

POULTRY LAYER FORMULA

| Component | lbs |
|---|---|
| Soybean meal | 280 |
| Corn, ground | 295 |
| Sorghum grain, ground | 300 |
| Dehydrated alfalfa | 25 |
| Sub-total | 900 |
| Premix A (pounds) | |
| Dicalcium phosphate | 25 |
| Limestone | 30 |
| Salt | 5 |
| Oyster shell (SPECIAL PULLET SIZE) | 30 |
| Sub-total | 90 |
| Premix B (grams) | |
| Vitamin A (10,000 IU/g) | 150 |
| Vitamin $D_3$ (15,000 IU/g) | 60 |
| Vitamin $B_{12}$ (20 mg/lb) | 120 |
| B-Complex (1233) | 450 |
| D-L Methionine | 350 |
| Trace minerals | 230 |
| Corn, ground | 3,180 |
| Sub-total (in lbs) | 10 |
| Total | 1,000 |

I claim:

1. In a process for preparing medicated animal feeds, feed additives, feed supplements or feed premixes, the improvement comprising
using in the process a tetracycline antibiotic, a sulfa drug, penicillin, monensin, tylosin or lasalocid or a mixture of the drugs by either
  (a) compacting the drug or mixture of drugs or
  (b) compacting a blend of the drug or mixture of drugs blended with a compressible and pharmaceutically acceptable inert diluent or diluent mixture with sufficient force to obtain a
    (1) compacted cdrug
    (2) compacted mixture of drugs
    (3) compacted blend of drug and diluent or diluents or
    (4) compacted blend of a mixture of drugs and a diluent or diluents
of at least about 10 kg to 30 kg hardness on a Stokes hardness tester and of a particle size range of 10 to 150 mesh to prevent excessive build-up, deposition, retention and dusting of the drug or mixture of drugs in the process.

2. A process according to claim 1 comprising
using in the process a sulfa drug by
  compacting the drug as described and
  blending the compacted drug with a pharmaceutically acceptable inert diluent or diluent mixture in amounts sufficient to total the medicated animal feeds, feed additives, feed supplements or premixes to 100%.

3. A feed supplement or feed premix process according to claim 2 comprising
using sulfamethazine in the process by
  compacting the sulfamethazine as described and
  blending the compacted sulfamethazine with other drugs and with a pharmaceutically acceptable inert diluent or diluent mixture in amounts sufficient to total the supplement or premix to 100%.

4. A process according to claim 1 comprising
using in the process a sulfa drug or a mixture of a sulfa drug and one or more of the additional drugs of claim 1 by
  compacting a blend of sulfa drug or a mixture of a sulfa drug and one or more of the additional drugs of claim 1 blended with a compressible and pharmaceutically acceptable inert diluent or diluent mixture.

5. A process according to claim 4 wherein a mixture of sulfamethazine or sulfathiazole and at least one additional drug of tylosin, chlortetracycline or a stable penicillin is used in the compacted blend.

6. A process according to claim 5 wherein the drug mixture comprises sulfamethazine, chlortetracycline and procaine penicillin G.

7. A process according to claim 5 wherein the drug mixture comprises sulfamethazine or sulfathiazole blended with tylosin or salts thereof.

8. A process according to claim 1 wherein the medicated animal feed supplement or premix preparation comprises: thoroughly blending 5% by weight to 65% by weight of the supplement or premix of a finely divided drug or a mixture of one or more finely divided drugs of tetracycline antibiotics, sulfa drugs or penicillin antibiotics with a compressible and pharmaceutically acceptable inert diluent or diluent mixture in amounts sufficient to total the supplement or premix to 100%; compacting the above blend with sufficient force to obtain compacted material of about 10 kg to about 30 kg hardness on a Stokes hardness tester; and grinding and sifting the compacted material to obtain a granular product of a particle size range of 10 to 150 mesh which is sufficiently large to avoid segregation or electrostatic adhesion and sufficiently small to assure statistically uniform distribution of the drugs in the finished feed and which is sufficiently hard to resist shattering, abrasion or crumbling.

9. A process according to claim 8 wherein the supplement or premix comprises: 16% by weight to 41% by weight of composition of chlortetracycline fermentation solids containing from 12% by weight to 27% by weight of chlortetracycline; 2% by weight to 6% by weight of composition of sulfamethazine; 2% by weight to 6% by weight of composition of procaine penicillin G; wherein the compacted material has a particle size range of 16 to 60 mesh.

10. A process according to claim 8 wherein the supplement or premix comprises: 32% by weight to 82% by weight of composition of chlortetracycline fermentation solids containing from 12% by weight to 27% by weight of chlortetracycline; 8% by weight to 13% by weight of composition of sulfamethazine; 7% by weight to 11% by weight of composition of procaine penicillin G; wherein the compacted material has a particle size range of 16 to 60 mesh.

11. A process according to claim 8 wherein the supplement or premix comprises: 25% by weight to 72% by weight of composition of chlortetracycline fermentation solids containing from 12% by weight to 27% by weight of chlortetracycline; and from 7% by weight to 10% by weight of sulfamethazine; wherein the compacted material has a particle size of 16 to 60 mesh.

12. A process according to claim 1 wherein the drug is penicillin.

* * * * *

UNITED STATES PATENT OFFICE
CERTIFICATE OF CORRECTION

Patent No. 4,447,421                     Dated May 8, 1984

Inventor(s) IRVING KLOTHEN

It is certified that error appears in the above-identified patent and that said Letters Patent are hereby corrected as shown below:

Column 14, Claim 1 line 42 delete [of] after "and" and before "a particle" and in place thereof insert --- *grinding and sifting the compacted material to* ---

Column 14, Claim 2 lines 47 and 48 delete [by compacting the drug as described]

Column 14, Claim 3 lines 56 and 57 delete [by compacting the sulfamethazine as described].

Signed and Sealed this

Fifth Day of March 1985

[SEAL]

Attest:

DONALD J. QUIGG

Attesting Officer

Acting Commissioner of Patents and Trademarks